United States Patent [19]

Gauthier

[11] 4,337,762

[45] Jul. 6, 1982

[54] SURGICAL RETRACTOR

[76] Inventor: William K. Gauthier, 400 Northline, Metairie, La. 70005

[21] Appl. No.: 122,619

[22] Filed: Feb. 19, 1980

[51] Int. Cl.³ ............................................ A61B 17/02
[52] U.S. Cl. ................................................... 128/20
[58] Field of Search ................ 128/15, 16, 17, 18, 128/19, 20, 11

[56] References Cited

U.S. PATENT DOCUMENTS

| 2,383,705 | 4/1943 | Bortagaray | 128/20 |
| 3,040,739 | 6/1962 | Grieshaber | 128/20 |
| 3,394,700 | 7/1968 | Yamamoto | 128/20 |
| 3,749,088 | 7/1973 | Gauthier | 128/20 |
| 3,965,890 | 6/1976 | Gauthier | 128/20 |
| 4,010,741 | 3/1977 | Gauthier | 128/20 |

Primary Examiner—Lee S. Cohen
Assistant Examiner—Nancy A. B. Swisher
Attorney, Agent, or Firm—Shoemaker and Mattare, Ltd.

[57] ABSTRACT

A surgical retractor includes an annular support ring and a unitary retractor arm movably attached thereto by a clamp. The clamp includes a captive nut and a stop on the arm prevents the clamp from becoming separated from the arm.

5 Claims, 3 Drawing Figures

SURGICAL RETRACTOR

BACKGROUND OF THE INVENTION

The present invention relates in general to surgical retractors, and, more particularly, to a surgical retractor which includes a frame having a plurality of retractor arms carried thereby with retractor blades carried by the arms and depending therefrom for placement in an incised wound to engage the flesh at the edges of the wound to pull the flesh out of the way of a surgeon during the performance of an operation.

Many different types of surgical retractors are known in the prior art, and the present invention is directed to those improvements in surgical retractors. The surgical retractor according to the present invention possesses several unique advantages over prior art devices.

For example, the retractor of the present invention is easily manufactured, and is easily assembled. The retractor has a minimum number of parts, and is thus easily sterilized.

SUMMARY OF THE INVENTION

The device of the present invention includes a unitary retractor arm releasably held on a support ring by a clamp.

The clamp has orthogonal openings which receive the ring and the arm so those two elements can be held together with the arm extending at essentially right angles to the ring at the point of attachment of those two elements.

The clamp includes a captive nut, and a stop on the arm prevents the clamp from accidentally becoming separated from the arm.

OBJECTS OF THE INVENTION

It is a main object of the present invention to provide a surgical retractor which is easily manufactured.

It is another object of the present invention to provide a surgical retractor which is easily sterilized.

These together with other objects and advantages which will become subsequently apparent reside in the details of construction and operation as more fully hereinafter described and claimed, reference being had to the accompanying drawings forming part hereof, wherein like reference numerals refer to like parts throughout.

DETAILED DESCRIPTION OF THE INVENTION

Figure 1:
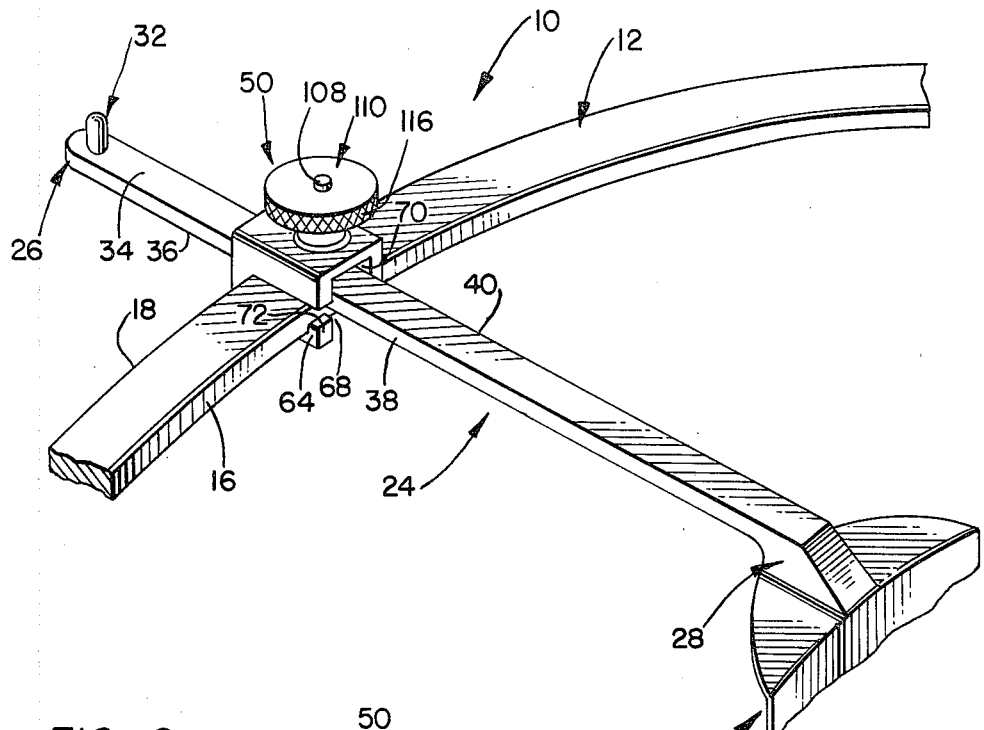
FIG. 1 is a perspective of a retractor embodying the teachings of the present invention.

Shown in FIG. 1 is a surgical retractor 10 which can be used to retain an incision in the open position while a surgeon proceeds with a surgical operation.

Figure 3:
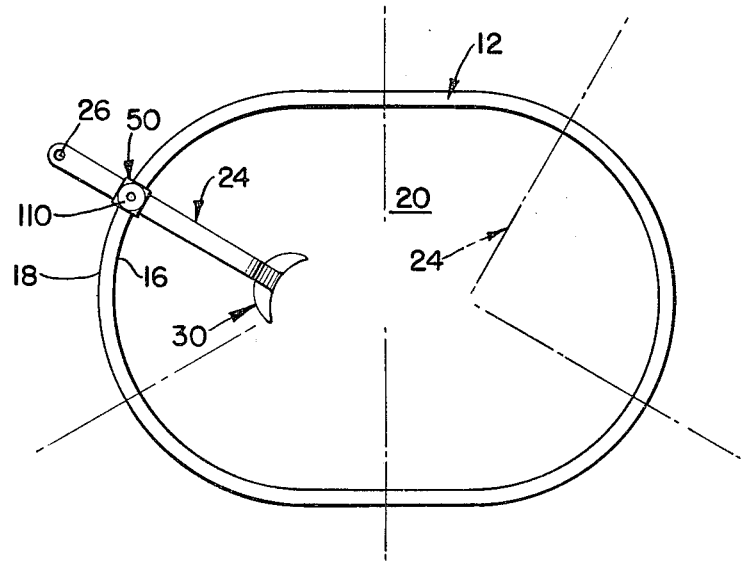
FIG. 3 is a top plan view of a retractor embodying the teachings of the present invention.

The retractor 10 is mounted on an annular support ring 12 which, as shown in FIG. 3, is in the shape of a prolate ellipse and has inner periphery 16 and outer periphery 18. The support ring is located adjacent an incision and has an open area 20 in which the surgeon operates.

The retractor includes an elongate unitary retractor arm 24 having one end 26 thereof curved, and having a depending boss 28 on the other end thereof. A retractor blade 30 is integrally attached to the boss 26 so that the blade and the arm are unitary. The blade 30 is fully disclosed in U.S. Pat. No. 3,749,088 and attention is directed to that patent for such disclosure. The disclosure of that patent is incorporated herein by reference thereto.

A stop 32 is located adjacent arm end 26 and extends upwardly from top surface 34 of that arm. The arm has lower surface 36 and longitudinal sides 38 and 40.

The retractor arm 24 is mounted on the support ring 12 by a clamp 50 to have the longitudinal centerline thereof located on a secant of that ring. As indicated by the phantom lines in FIG. 3, a plurality of retractor arms can be simultaneously mounted on the ring 12.

Figure 2:
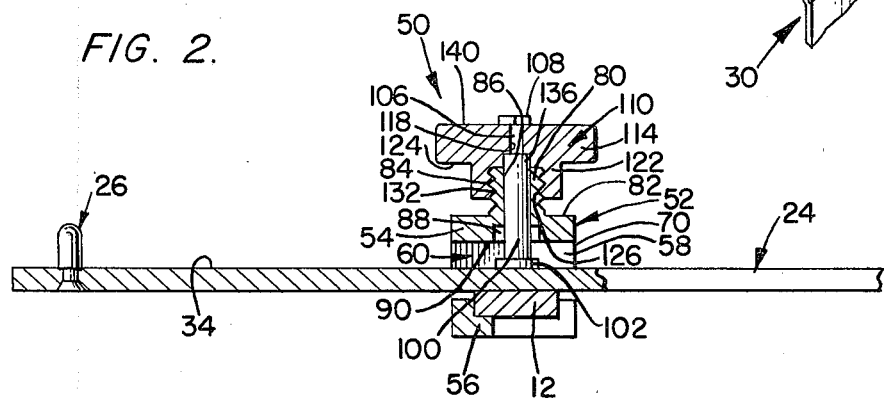
FIG. 2 is a partially cut away side elevation of a retractor embodying the teachings of the present invention.

A clamp 50 is best shown in FIG. 2 to include a C-shaped body 52 having a top leg 54 and a bottom leg 56 integrally joined together by a web 58. The top and bottom legs are separated from each other by a gap 60 which is sized to accommodate the support ring with the retractor arm positioned thereon as shown in FIG. 1.

The clamp bottom leg is U-shaped with leg 64 being unitary with the clamp web and being spaced apart from a corresponding leg by a semicircular gap 68. Arm receiving openings, such as openings 70, are defined in the clamp. One of the openings is defined in the web 58, and is preferably rectangular in shape. Projections, such as projection 72, are located on the legs 64 to abut the support ring inner periphery 16 and to thereby prevent the clamp from accidentally separating from the support ring.

An upstanding tubular projection 80 is integrally mounted on top surface 82 of the clamp top leg 54 to be unitary therewith. The projection has screw threads 84 on the outside surface thereof and a bore 86 defined longitudinally therethrough. A seat 88 is defined in undersurface 90 of the top leg 54 to be coaxial with the bore 86.

A cylindrical clamping rod 100 is received in the bore 86 to be slidable longitudinally thereof. The rod 100 includes a step bearing, or clamping foot 102 on one end thereof and a mounting shaft 106 on the other end thereof. A stop 108 is integrally mounted on the end of shaft 106 which is remote from the rod 100. The seat 88 is sized to receive the clamping foot 102.

A captive nut 110 is mounted on the rod 100 and includes a circular body 114 having knurling 116 on the peripheral edge thereof and a bore 118 extending centrally and axially therethrough. A coupling sleeve 122 is integrally attached to lower surface 124 of the nut to be unitary therewith. The sleeve includes a bore 126 defined longitudinally thereof and has screw threads 132 on the inner surface thereof. The screw threads 132 cooperate with the screw threads 84 to draw the nut down onto the projection 80 during a clamping procedure.

A counterbore 136 is defined in the nut to be axially aligned with the bores 118 and 126. The clamping rod 100 is received in the counterbore 136, and the mounting shaft 106 is received in the bore 118 as best shown in FIG. 2.

Top surface 140 of the nut abuts the stop 108, and the nut is rotatably held on the clamping rod 100 thereby.

However, the nut cannot be removed from the clamp, thereby preventing the nut from accidentally falling off.

As shown in FIG. 2, the arm 24 is received through the aligned openings 70, and the support ring is received through the gap 60 to orient the arm essentially perpendicularly with respect to the ring. The captive nut is rotated, thereby forcing the clamping rod downwardly to force the clamping foot against the retractor arm. The clamp is mounted on the support ring so the retractor arm is on top of the support ring which is captured between the projections 72 and the web 58 thereby securely clamping the retractor arm to the support ring. The stop 32 prevents the clamp from accidentally sliding off the retractor arm.

The retractor arms are positioned on the support ring in any desired location and the clamps are operated to securely hold those arms in those locations. The arms can be retracted radially outward of the support ring to retract an incision by loosening the clamps slightly. The retractor blades are operated as discussed in the referenced patent.

The retractor 10 is manufactured from an autoclavable material, and the arm is unitary and thus easily manufactured in a casting or molding process. The clamp is also easily manufactured in a casting or molding process.

As this invention may be embodied in several forms without departing from the spirit or essential characteristics thereof, the present embodiment is, therefore, illustrative and not restrictive, since the scope of the invention is defined by the appended claims rather than by the description preceding them, and all changes that fall within the metes and bounds of the claims or that form their functional as well as conjointly cooperative equivalents are, therefore, intended to be embraced by those claims.

I claim:

1. A surgical retractor comprising:
   an annular support ring;
   a unitary one-piece retractor arm having a retractor blade integrally mounted thereon at one end of said arm and a stop on another end of said arm; and
   a unitary, integral clamp coupling said retractor arm to said support ring, said clamp including a unitary one-piece C-shaped body having a pair of legs at one end of said C-shaped body, and having ring accommodating openings therethrough and arm accommodating openings therethrough, said ring and arm accommodating openings being oriented at a right angle with respect to each other so that said arm is oriented at a right angle with respect to said support ring when said arm is held on said ring by said clamp, said clamp body including abutment means on said legs abutting the inner periphery of said support ring to prevent said clamp from separating from said support ring, whereby said clamp allows engagement of both the ring and arm members with one locking member; said clamp further including a projection extending upwardly therefrom and having a bore defined therethrough, said clamp further including a rod extending through said bore for contacting at one end thereof said retractor arm and a captive nut on another end of said rod, said captive nut and said projection having first coupling means thereon for attaching said nut to said projection, said captive nut and said rod having further coupling means thereon for forcing said rod one end against said retractor arm, said clamp having support ring capture means for holding said ring in said clamp, said retractor arm being sandwiched between said rod one end and said support ring so that said retractor arm is securely held on said ring by said clamp.

2. The surgical retractor defined in claim 1 further including knurling on said captive nut.

3. The surgical retractor defined in claim 2 wherein said first coupling means includes a threaded coupling.

4. The surgical retractor defined in claim 3 further including a stop on another end of said rod holding said captive nut on said rod.

5. The surgical retractor defined in claim 4 wherein said support ring is in the shape of a prolate ellipse.

* * * * *